United States Patent [19]

DeVido et al.

[11] Patent Number: 5,254,161
[45] Date of Patent: Oct. 19, 1993

[54] THERMALLY STABLE NITROCELLULOSE EMULSIONS, SOLUTIONS AND COATINGS

[75] Inventors: John P. DeVido, Kennett Square, Pa.; Ernest C. Linsay, Hockessin; Daniel M. Zavisza, Newark, both of Del.

[73] Assignee: Aqualon Company, Wilmington, Del.

[21] Appl. No.: 781,839

[22] Filed: Oct. 24, 1991

[51] Int. Cl.$^5$ .................................... C09D 101/18
[52] U.S. Cl. .................... 106/170; 106/176; 106/195; 106/198
[58] Field of Search ............... 106/170, 176, 195, 198

[56] References Cited

U.S. PATENT DOCUMENTS

| | | | |
|---|---|---|---|
| 4,022,724 | 5/1977 | Kreuder et al. | 260/16 |
| 4,515,633 | 5/1985 | Cruz, Jr. | 106/18.28 |
| 4,590,019 | 5/1986 | Luhmann et al. | 264/3.4 |
| 4,657,590 | 4/1987 | Gamblin | 106/22 |
| 4,814,015 | 3/1989 | Quinlan | 106/189 |
| 4,900,621 | 2/1990 | Kohn | 428/333 |
| 4,902,301 | 2/1990 | Rogers et al. | 23/302 |
| 4,937,281 | 6/1990 | Tang | 524/517 |
| 4,954,619 | 9/1990 | Lang et al. | 536/20 |

FOREIGN PATENT DOCUMENTS

| | | |
|---|---|---|
| 0353477 | 2/1990 | European Pat. Off. |
| 76076 | 9/1970 | German Democratic Rep. ................ 106/189 |

OTHER PUBLICATIONS

"Nitrocellulose", Hercules Powder Co., 1944, No. 500-256-4M-9.46.
Hawley, *Condensed Chemical Dictionary*, Van Nostrand Reinhold Co., N.Y., 1973, pp. 285, 455-456.

*Primary Examiner*—David Brunsman
*Attorney, Agent, or Firm*—James K. Luchs; David Edwards

[57] ABSTRACT

Emulsions, solutions and coatings comprising nitrocellulose are stabilized against yellowing on thermal aging when treated with boric acid or borax or hydrogen peroxide or 0.1 to 0.5% by weight of a chlorinated hydantoin such as 1,3-dichloro 5,5-dimethylhydantoin (DCH). Boric acid or borax may be added as aqueous solutions during nitrocellulose manufacture. Combined treatments and/or additions of boric acid and DCH give optimum stabilization against yellowing.

13 Claims, No Drawings

THERMALLY STABLE NITROCELLULOSE EMULSIONS, SOLUTIONS AND COATINGS

FIELD OF THE INVENTION

This invention relates to nitrocellulose products used in the form of emulsions and solutions for coatings. In particular the invention relates to nitrocellulose emulsions and solutions for coatings which exhibit reduced yellowing.

BACKGROUND OF THE INVENTION

Nitrocellulose was once widely used for automotive finishes. Henry Ford had said "Give them any color they want as long as it's black." This was significant since a black nitrocellulose car finish did not show yellowing on aging. It was this problem with yellowing which led to the phase out of nitrocellulose for auto finishes as consumers demanded more than basic black.

Yellowing continues to be a problem in nitrocellulose uses for furniture lacquers and clear nail polish.

Technological advances continued even though nitrocellulose yellowing was not addressed. The development of an improved nitrocellulose manufacturing process is described in U.S. Pat. No. 4,590,019. A water based nitrocellulose spray paint is described in European Patent Application 0 353 477 A1. U.S. Pat. No. 4,900,621 discloses pinhole-free nitrocellulose coatings. U.S. Pat. No. 4,954,619 discloses an improved film forming nitrocellulose nail polish.

U.S. Pat. No. 4,022,724 discloses the use of bis-hydroxyphenyl-3-alkanes for prevention of yellowing. It would appear from U.S. Pat. No. 4,937,281 that a need existed for non-yellowing clear acrylate coatings similar to the unresolved problem with nitrocellulose yellowing.

Thus, an unsatisfied need existed prior to the present invention to prevent yellowing when nitrocellulose was manufactured and used in the form of solution, emulsion or coating.

SUMMARY OF THE INVENTION

It is an object of the invention to provide a nitrocellulose composition in the form of a coating solution or emulsion, characterized in that the composition exhibits reduced yellowing during aging wherein the composition comprises an effective amount of hydrogen peroxide or boric acid or an alkali metal salt of boric acid and/or a chlorinated hydantoin having the following structure:

wherein X can be Cl or Br,
where $R_1$ and $R_2$ can be hydrogen or methyl groups.

The preferred compound (1,3-dichloro-5,5-dimethylhydantoin) has the structure:

A preferred nitrocellulose composition for furniture lacquer or clear nail polish coating comprises at least one of:

(a) boric acid or borax; and
(b) 1,3-dichloro-5,5-dimethylhydantoin (DCH);
wherein a coating composition or a coating containing one or both of these exhibits lower yellowing on thermal aging.

It is a further object of the invention to provide a manufacturing process for improving the thermal stability of a nitrocellulose composition comprising the steps:

(1) producing an unstabilized nitrocellulose in an aqueous medium;
(2) mixing the nitrocellulose in an aqueous medium containing dissolved boric acid or borax ($Na_2B_2O_3 \cdot 10 H_2O$) for a time sufficient for the nitrocellulose to absorb a stabilizing amount of boric acid or borax; and
(3) recovering a stabilized nitrocellulose product suitable for preparing a furniture lacquer or clear finger nail polish.

Combined treatments and/or additions of borax and DCH are preferred for optimum benefit against yellowing.

DETAILED DESCRIPTION OF THE INVENTION

U.S. Pat. No. 4,937,281 describes the use of ultraviolet stabilizers to prevent yellowing in acrylate coatings. While it would appear that such technique might similarly apply to nitrocellulose yellowing, it was in fact discovered that thermal stability was the major problem requiring a solution. Finding such a solution was the advance in the state of the art provided by the invention.

It was indeed a surprising and unexpected result to find how simply and effectively both classes of additives worked, and further that boric acid and borax could be incorporated during the nitrocellulose manufacturing process. This advance is further significant in view of the length of time that this yellowing problem had existed without clues to any solution prior to the present invention.

It has been discovered that activity for prevention of yellowing can vary as structural changes are made to the hydantoin, for example Most Active Less Active

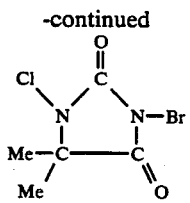

While 1,3-dichloro-5,5-dimethylhydantoin (DCH) is preferred, other suitable compounds include N-chlorosuccinimide. Effective amounts of additions are from 0.2 to 5.0% by weight based on the weight of the nitrocellulose. Preferred amounts are from 0.4 to 2.0% by weight.

While hydrogen peroxide solutions and boric acid and borax ($Na_2B_2O_3 \cdot 10 H_2O$) are preferred as water soluble additions, other alkali metal salts such as potassium borate and lithium borate could be employed. Effective amounts of additions are from 0.1 to 5.0% by weight based on the weight of nitrocellulose. Preferred amounts are from 0.8 to 1.0% by weight.

Stabilized nitrocellulose can be produced by a novel manufacturing process wherein water soluble boric acid and/or borax can be added during a washing step concurrent with nitrocellulose manufacture.

A preferred process involves the steps:
(1) producing a fibrous form of unstabilized nitrocellulose in an aqueous medium;
(2) mixing the nitrocellulose with a solution of boric acid during a washing step and allowing the nitrocellulose to equilibrate at 40° C. for at least 30 minutes; and
(3) decanting the now stabilized nitrocellulose to produce a product slurry suitable for further treatment and formulation to prepare a lacquer or a clear fingernail polish.

During step (2) approximately 1 liter of a 0.5% by weight boric acid solution is used to treat 450 g of solid nitrocellulose. While elevated temperature might increase the rate of adsorption of the boric acid onto the nitrocellulose, this is not a recommended technique due to potential exothermal excursions which have been known to occur during nitrocellulose manufacturing processes.

The invention which has applicability for industrial, home and personal use coatings is illustrated by the following examples.

EXAMPLE 1

An aqueous nitrocellulose/acrylate emulsion was prepared according to the techniques described in U.S. Pat. Nos. 3,953,386 and 4,011,388 except that sodium hydroxide was used in place of sodium bicarbonate. With and without additions according to the invention, control and experimental formulations were drawn down onto white glass plates to prepare test coatings. These coatings were aged at 150° F. (66° C.), and yellowing was followed by periodically measuring Yellowness Index (YI). Table 1 contains comparative results of the testing.

TABLE 1

| Addition | % Addition | YI Initial | 150° F. YI 24 Hrs. | 150° F. YI 48 Hrs. |
|---|---|---|---|---|
| Control | — | 6.66 | 22.48 | 26.86 |
| DCH | 0.2 | 2.43 | 10.46 | 12.27 |
| Boric Acid | 0.5 | 4.92 | 8.02 | 10.09 |

TABLE 1-continued

| Addition | % Addition | YI Initial | 150° F. YI 24 Hrs. | 150° F. YI 48 Hrs. |
|---|---|---|---|---|
| DCH + Borax | 0.2 + 0.5 | 3.90 | 6.05 | 8.09 |

As shown, the best protection against yellowing on thermal aging involved the DCH and boric acid combination.

EXAMPLE 2

A solvent nitrocellulose lacquer was prepared using the following formulations:

| | |
|---|---|
| Nitrocellulose ½ sec. (IPA wet) | 750 g |
| Ethanol 2B | 107 g |
| Butanol | 172 g |
| Xylene | 770 g |
| Methylethylketone (MEK) | 259 g |
| Butyl acetate | 548 g |
| Exxate ® 600 (Exxon Chemicals) | 51 g |

Dried coatings were thermally aged by first being tested for 44 hours at 1500° F. followed by 47 hours at 1800° F. Results are shown in Table 2.

TABLE 2

| Addition | Initial YI | YI After Therm. Aging |
|---|---|---|
| Control | 2.69 | 8.09 |
| DCH | 1.32 | 5.58 |

As shown, DCH gives superior protection under thermal aging.

EXAMPLE 3

Example 1 was repeated except that either borax or hydrogen peroxide was substituted for boric acid. Similar results were obtained, but hydrogen peroxide gave slightly less yellowing protection than DCH.

EXAMPLE 4

Example 1 was repeated except that the water wet nitrocellulose was manufactured with different viscosity, which varied from ¼ sec. to ½ sec. Equivalent prevention of yellowing was obtained with DCH, borax or boric acid and combinations thereof. Slightly poorer protection was provided when hydrogen peroxide was used in from 1% to 5% by weight based on the weight of nitrocellulose.

EXAMPLE 5

Example 1 was repeated except that a bromo-chlorohydantoin was substituted for DCH. This was less effective at equivalent addition levels to DCH, but it was suitable for providing significant protection from thermal aging yellowing for either an emulsion or a coating.

COMPARATIVE EXAMPLE 6

Materials tested in the same manner as DCH which proved to be ineffective against yellowing on thermal aging were:

N-bromosuccinimide, N-bromoacetamide, trichloromelamine, trichloroisocyanuric and, N-bromophthalimide, azobisisobutyronitrile, benzophenone, dicumylperoxide, mixture of para and meta isomers of alpha, alpha'-bis(t-butylperoxy)diisopropylbenezene, MEK peroxide, and t-butylhydroperoxide.

EXAMPLE 7

Example 3 was repeated except that benzoyl peroxide was substitited for hydrogen peroxide. Similar reduced yellowing was observed.

What is claimed is:

1. A nitrocellulose composition in the form of a coating, solution or emulsion, characterized in that the composition exhibits reduced yellowing during aging wherein the composition comprises nitrocellulose and an effective amount of one or more of borax or a chlorinated hydantoin having the following structure:

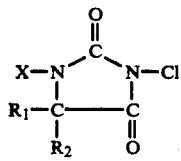

wherein X can be Cl or Br, and where $R_1$ and $R_2$ can be hydrogen or methyl groups.

2. The nitrocellulose composition of claim 1 where the composition includes the chlorinated hydantoin that is 1,3-dichloro-5,5-dimethylhydantoin (DCH) with the structure:

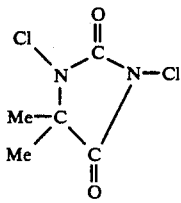

added in an amount of 0.2 to 5.0% by weight based on the weight of nitrocellulose.

3. The composition of claim 2, further characterized in that the composition contains 0.4 to 2.0 weight percent DCH based on the weight of nitrocellulose.

4. The composition of claim 1 where boric acid or borax are added to an aqueous nitrocellulose system.

5. The composition of claim 1, further characterized in that the composition contains 0.01 to 0.50 weight percent boric acid or borax based on the weight of nitrocellulose.

6. A process for improving the thermal stability of a nitrocellulose composition comprising the steps
   (1) producing an unstabilized nitrocellulose in an aqueous medium,
   (2) mixing the nitrocellulose in an aqueous medium containing dissolved boric acid or borax for a time sufficient for the nitrocellulose to adsorb a stabilizing amount of boric acid or borax for at least 30 minutes at 40° C.,
   (3) recovering a stabilized nitrocellulose product suitable for preparing a coating composition.

7. A nitrocellulose protective or decorative coating comprising nitrocellulose and an organic solvent, characterized in that the nitrocellulose is stabilized against yellowing on thermal aging with DCH or borax or hydrogen peroxide.

8. The coating of claim 7 where the nitrocellulose is contained in a nitrocellulose lacquer.

9. The coating of claim 8 containing from 1 to 5% by weight hydrogen peroxide based on the weight of nitrocellulose.

10. The coating of claim 7 where the nitrocellulose is contained in a nitrocellulose/acrylate or nitrocellulose lacquer emulsion.

11. The coating of claim 7 where the nitrocellulose is contained in a nail polish composition.

12. The coating of claim 7 containing from 0.8 to 1.0% by weight borax or boric acid based on the weight of nitrocellulose.

13. The coating of claim 7 containing from 0.4 to 2.0% by weight DCH based on the weight of nitrocellulose.

* * * * *